United States Patent [19]

Weiss et al.

[11] 3,968,695

[45] July 13, 1976

[54] DEVICE FOR TAKING SAMPLES OF MOLTEN METALS FLOWING IN PIPES

[75] Inventors: Hansjakob Weiss, Bensberg; Dieter Cremer, Bensberg-Immekeppel; Eginhard Kranz, Cologne, all of Germany

[73] Assignee: Interatom Internationale Atomreaktorbau GmbH, Bensberg, Cologne, Germany

[22] Filed: Aug. 28, 1975

[21] Appl. No.: 608,702

[30] Foreign Application Priority Data

Sept. 11, 1974 Germany.............................. 2443559

[52] U.S. Cl............................................. 73/422 R
[51] Int. Cl.².......................................... G01N 1/10
[58] Field of Search...................... 73/422 R, DIG. 9

[56] References Cited
UNITED STATES PATENTS

| | | | |
|---|---|---|---|
| 3,872,718 | 3/1975 | Nelson et al. | 73/422 R |
| 3,881,355 | 5/1975 | Nelson et al. | 73/422 R |

*Primary Examiner*—S. Clement Swisher
*Attorney, Agent, or Firm*—Kenyon & Kenyon Reilly Carr & Chapin

[57] ABSTRACT

A device is described for taking samples from a liquid-metal-carrying pipe loop, in which the flowing liquid metal is a hot molten metal and may also be radioactive, e.g., metal in a main coolant loop of a sodium-cooled nuclear reactor. The device is suited for in-line as well as out-line operation and uses the conventional crucibles. The crucibles are arranged in a vertical housing in a circle around a vertical feed line for the liquid metal and extending upwardly into the housing. The liquid metal flowing into the device from the feed line's upper end, is deflected downwardly into the crucibles by a downwardly facing concave baffle surface which is concentric with the feed line. The crucibles can be taken out of the device, hanging on an insert forming a closure for the housing's top and that can be unscrewed and lifted, to obtain the crucibles. Improved arrangements of the thermocouples used for measuring the temperature of the liquid metal, and of the electric system required for heat the device are disclosed.

14 Claims, 2 Drawing Figures

3,968,695

DEVICE FOR TAKING SAMPLES OF MOLTEN METALS FLOWING IN PIPES

BACKGROUND OF THE INVENTION

The present invention concerns a device for taking samples from a pipe loop carrying flowing liquid metal, particularly hot molten metal, consisting of a housing with inlets and outlets for the liquid metal, in which crucibles are arranged that can be filled with the liquid metal and taken out of the housing. The operational safety and efficiency of plants using such liquid metal, particularly of sodium-cooled nuclear power plants, depend heavily on the purity of the liquid metal, as impurities in the form of oxides form deposits which are hard to remove from equipment and which may, for instance, affect the functioning of valves adversely. Contamination by carbon can lead to carburization and corresponding embrittlement of the structural material used. It is therefore necessary to take samples of the metal at regular intervals, which samples can be analyzed for the presence of such impurities. Such an analysis can, of course, also serve for the determination of other substances, e.g., hydrogen. It is practical to fill the liquid-metal samples into crucibles, such as are commonly used in chemical laboratories. To ensure reliable analytical results, it is necessary to maintain a definite degree of filling of the crucibles and to prevent further impurities from penetrating into the samples while being taken. The samples should also be representative of the composition of the entire quantity of liquid metal, so that it is advisable to take it from a loop circuit, in which the liquid metal flows.

The analysis itself is usually performed in such a manner that the liquid itself, which is contained in the crucibles, e.g., sodium, is distilled off and the then remaining residue is examined chemically. Taking samples is made difficult to no small degree by the high temperatures prevailing in liquid-metal installations. If the liquid-metal is the coolant in a nuclear power plant, the liquid metal is more or less radioactive and requires a special design of the sampling apparatus as well as increased precautions in handling the samples.

Apparatus for taking samples from a loop carrying liquid sodium has been described in "Journal of Nuclear Energy", vol. 24 (1970), pages 503 to 508. On pages 607 and 608 of the same journal, further improvements of this apparatus have been proposed, which are to make it suitable for so-called in-line operation, explained below. However, certain shortcomings are inherent in this and other known apparatus of similar kind.

Besides the fact that these prior art embodiments are in general poorly suited for molten metal and that their design is not advantageous for obtaining the vacuum required for the distillation, they have the shortcomings listed as follows: large inside surfaces, at which radioactive residue can form; poor flushing-out of the crucibles, which may make the samples taken unrepresentative, and inaccurate measurement of the temperature of the liquid metal because of the unfavorable arrangement of the thermocouples used for this purpose.

An accurate temperature measurement is important, however, for an exact evaluation of the results of the analysis. It is also doubtful that the desired filling level of the crucibles can be kept accurately with apparatus of the prior art type. In addition, operation is rather awkward, necessitating detaching interfastened flanges connecting the sampling device with the pipe installation, and transporting the entire apparatus to the laboratory. From the German Offenlegungsschrift No. 1,955,988, an improved apparatus of the same type is known which, however, still does not meet all the requirements set forth above. There, the further processing of the samples after they are taken is discussed also.

An object of the present invention is an improved device for taking liquid-metal samples, particularly of molten sodium, where the latter may also be radioactive, and which due to its design adapts the device to the properties of such metal and provides representative samples of the same in a simple and safe manner.

SUMMARY OF THE INVENTION

To solve this problem, the broad concept is to have a feed line for the liquid metal extend vertically upward into a vertical, cylindrical housing and to have the feed line end centrally in the housing and at a distance from a downwardly facing, annular concave baffle surface forming the upper wall of the housing and concentric with the feed line, and to arrange the crucibles in the area of a ring-shaped zone concentrically around the feed line and below the baffle surface. In addition to a particularly space-saving design, this embodiment has in particular the advantage that liquid metal is admitted in the form of an annular downward flow symmetrically to all crucibles in the same manner, and that the latter can be thoroughly flushed by being filled to overflowing, before the samples proper are taken.

In a specific embodiment of the invention, the crucibles are disposed in mounts which are suspended from the upper wall of the housing, in a manner such that perfectly horizontal alignment of the crucibles and, therefore, their constant degree of filling is ensured. The crucibles nevertheless remain easily removable. The liquid metal overflowing from the crucibles after the flushing, can downwardly flow off freely through spaces between the mounts.

The concave baffle surface is made with rotational symmetry with respect to the other parts, so that uniform admission of the liquid metal to all of the crucibles is assured.

In a further embodiment of the invention, the upper wall of the housing is a removable insert which can, for example, be unscrewed. The insert with the mounts suspended from it and the crucibles held in them, can thus be pulled upwardly relatively simply into a so-called manipulator box, where the crucibles are taken from the mounts and packaged in a vacuum-tight and, if indicated, radiation-protected manner for shipment to the laboratory.

The annular concave baffle has a downwardly pointing, conical, central portion defining with the concave portion a peripheral, liquid stream, run-off inner edge for the liquid metal, such a run-off edge also being formed as an outer edge by the outer periphery of the baffle, the two edges being radially spaced apart. If both edges radially span fully the radial extent of the previously referred-to annular zone within which the upper peripheries of the crucibles are encompassed, a solid annular stream of liquid metal falls directly into the crucibles. However, by making one of those run-off edges radially off-set, as by reducing the diameter of the annular, concave baffle, for example, one run-off edge can be offset inwardly with respect to the center of the aforesaid annular zone, so that the descending annular liquid metal stream is offset correspondingly with respect to the crucible's peripheries, thus causing the descending liquid metal to swirl in the crucibles, for thoroughly initial flushing of the crucibles.

In a specific embodiment of the invention, all inside surfaces of the housing are declined against the horizontal and are without sharp corners as by having rounded surfaces. Sharp corners should be avoided in the device as far as possible in order to prevent the formation of droplets which can falsify the results of the analysis if they later drop into the crucible, and they also increase unnecessarily the quantity of the possibly radioactive liquid metal remaining in the device. Also, such drops can leave residue during distilling, if done in the device, which gradually increases when the device is used repeatedly.

In a specific embodiment of the device according to the invention for radioactive liquid metal, it is proposed that the removable insert has a space filled with a radiation-impervious substance, preferably in the direction from which the device is operated by personnel. The radiation-impervious substance may be, for instance, lead oxide in granular form.

In the preceding, it is assumed that the device is to be used in so-called out-line operation, i.e., the filled crucibles are taken from the device, transported to the laboratory and the liquid metal is distilled off only there for analyzation of any residue, by means of suitable apparatus. For operational and safety reasons, however, it is desirable and has already been proposed in the cited journal, to perform the distilling-off of the liquid metal in the device itself and take from it only the empty crucibles which contain such residue as may remain after the distilling-off.

To obtain the temperature required for such distillation, an electric heater arranged helically around the housing of this new device can be used in the manner known per se, while additional cooling of the surfaces intended for the condensation of the distillate (for instance, by means of an Na-K eutectic) can be dispensed with, contrary to former opinion, by performing the condensation of the liquid-metal vapor in a separate vessel. However, to obtain uniform quality of the samples, an isothermal temperature pattern is necessary in the region of the crucibles, which cannot automatically be obtained with an electric heating coil wound with constant pitch wound around the device's housing. In a further embodiment of the invention, it is therefore proposed to make the pitch of the heater helix or coil non-uniform according to the local heat requirements. In a specific embodiment of this idea of the invention, it is proposed that the pitch of the heater helix is large at the height of the crucibles and small below and above.

To equalize the non-uniform temperature magnitude caused by the heat convection, it is proposed according to a further feature of the invention to make the pitch of the heater helix larger above the crucibles than below them.

Maintaining tightness between the housing and the removable insert sufficient for the existence of the distillation vacuum, requires special measures to prevent inaccurate placement of the mutual sealing surfaces against each other, due to possibly present deposits. To avoid this drawback, it is proposed according to the invention to clad the sealing surfaces between the housing and the removable insert with a hard, wear-resistant alloy such as "Stellite", a trademark for an alloy consisting essentially of 75–90% cobalt and 10–25% chromium, so that they can be pressed together so strongly that the residue is pushed away from the sealing surfaces.

For the same purpose at least one of the sealing surfaces can be made crowned.

While other parameters of interest for evaluating the analysis, such as the flow rate and the time used for flushing out the crucibles, can be measured outside the device, it is desirable to measure the temperature of the liquid metal as closely as possible to the crucibles. Thermocouples are particularly well suited as the temperature measuring devices for this purpose. In order to bring them as close to the liquid-metal samples, in the crucibles, as possible, a further feature of the invention is to solder the thermocouples into the crucible mounts. The wires can be led here through vertical columns supporting the crucible mounts depending from the removable insert. As an alternate or an addition thereto, it is proposed that the thermocouples are arranged in the depending conical part of the baffle, which can protrude into the feed line.

BRIEF DESCRIPTION OF THE DRAWINGS

An example of an embodiment of the invention is shown in the drawings, where.

DETAILED DESCRIPTION OF THE INVENTION

Figure 1:
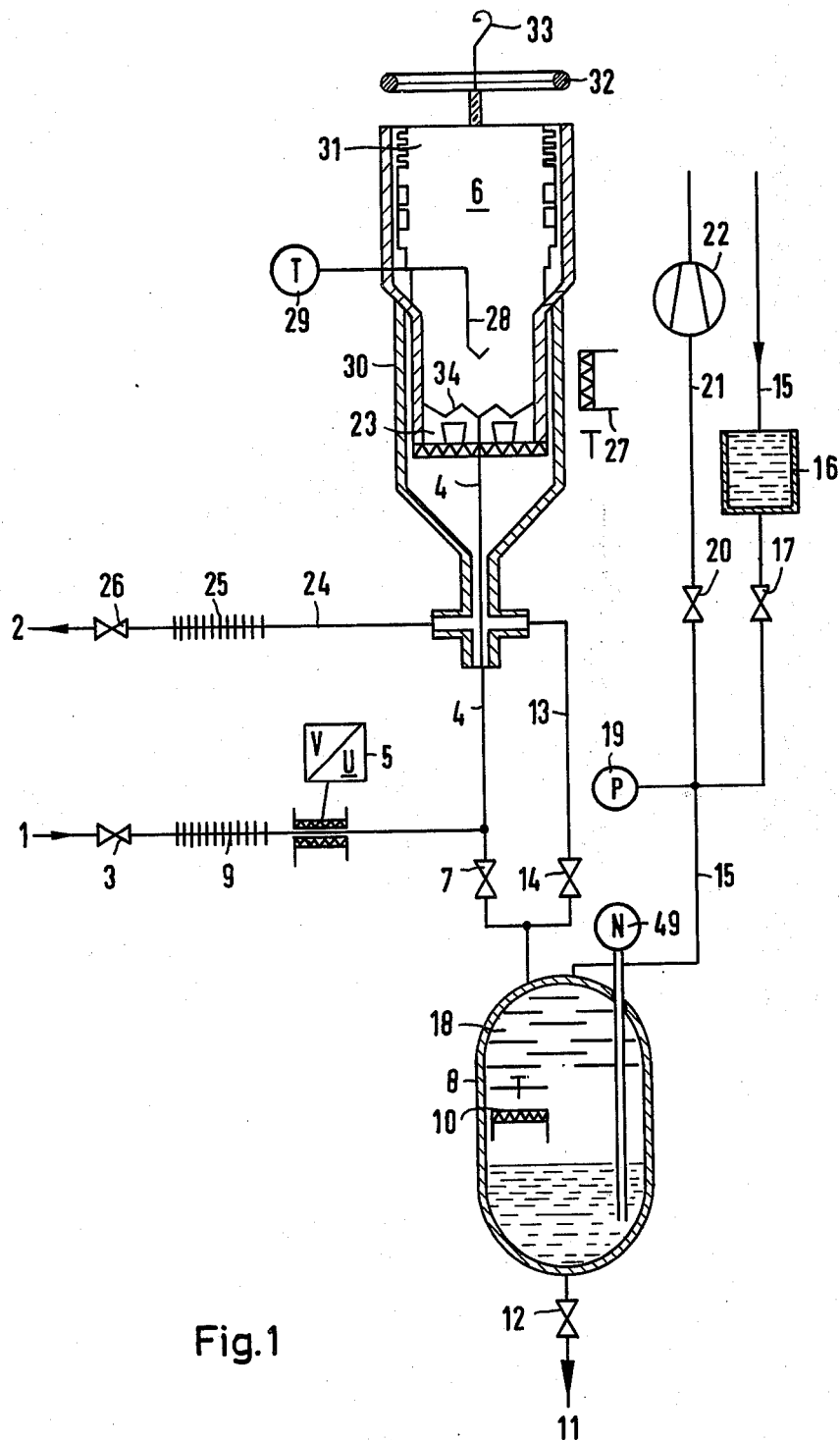
FIG. 1 shows in vertical section a schematic overall view of the device and the auxiliary arrangements required for its operation, and FIG. 2, on an enlarged scale and in section, part of the device itself.

A stream of liquid metal, whose flow rate is monitored by a flow meter 5, is taken from the flowing metal to be sampled, through a line 1. The line can be shut off by means of a valve 3 and can furthermore be closed by freezing the liquid metal by means of a cooling section 9. The line 1 divides into the two branches of a further line 4 which leads on the one side to sampling device 6 of the present invention and on the other side, with the provision for being shut off by a further valve 7, to a buffer tank 8. The last-mentioned connection serves mainly for letting off the liquid metal from the sampling device 6 and is closed in normal operation. The buffer tank 8 is equipped with a controllable electric heating system 10 and a liquid-level measuring device 49. The buffer tank can be drained via a line 11 which can be shut off by a further valve 12, to a suitable draining tank (not shown) and this tank has a further line 13 which can be shut off by a further valve 14 and which leads likewise to the sampling device 6. The part of the buffer tank 8 not filled with the liquid metal is filled via a further line 15, with a protective gas which is inert to the liquid metal and is purified in a suitable device 16 and flows via a further valve 17 and through a sodium vapor trap 18 into the buffer tank 8. The control of the gas pressure is ensured by a pressure-measuring device 19. Into the line 15 opens a further line 21, which can be shut off by a further valve 20 and which leads to a vacuum pump 22. With the valves 3, 17, 26 closed, and 7, 14 20 open, the interior of the sampling device 6 can be evacuated by means of the vacuum pump 22, as is necessary for distilling off the liquid-metal samples contained there in the crucibles 23.

Figure 2:
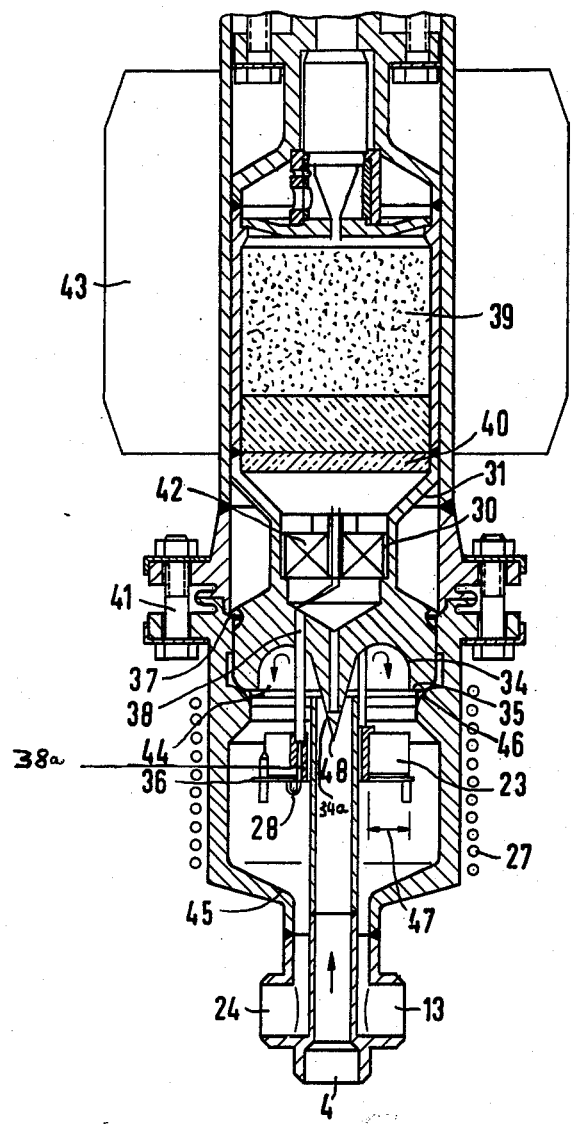

The liquid metal gets into the crucibles 23 via the line 4, with the valve 3 open and the valve 7 closed, in the manner shown in detail in FIG. 2, the excess flowing off via a further line 24, which is likewise equipped with a cooling section 25 and can be shut off by a further valve 26. The sampling device 6 comprises, otherwise, a controllable electric heating system 27 and thermocouples 28, which latter are brought to a temperature measuring device 29 situated on the outside of the device 6.

The sampling device 6 consists essentially of a cylindrical housing 30, into which a removable, cylindrical insert 31 is screwed, for instance, by means of a hand wheel 32, this insert having depending means supporting the crucible mounts 36. At its upper end, the insert 31 is provided with a suspension device or hook 33. By means of the hook and a lifting device (not shown), the insert 31 with the crucibles 23 on the mounts 36, can be pulled upwardly and into one of the known manipulator boxes, also not shown here, where the crucibles are removed and packed for shipment to the chemical laboratory.

FIG. 2 shows more clearly how the liquid metal fed-in via a vertical line 4 is deflected at the upper open end of the latter, by an annular, downwardly facing concave baffle surface 34 formed in the bottom of the insert 31, and thus guided into the crucibles 23. The baffle surface 34 is provided here with a run-off edge 35 which ensures that the liquid-metal stream flows into the crucibles 23 in such a manner that it causes strong turbulence there and causes a thorough flushing of the same. This is achieved best by arranging the crucibles inside a ring-shaped zone 47, and the run-off edge 35 over the outer edge of this zone. The crucibles 23 are disposed in horizontal mounts 36 which are suspended from the insert 31 by vertical columns 38. In the columns 38, the wires 28a of the thermocouples 28 are led up to the mounts 36 and soldered there to the mounts. For the protection of the operating personnel, the insert 31 is filled at its upper end with a radiation-impervious substance 39, e.g., granulated lead oxide. Thermal insulating material 40 serves as heat protection, for instance, for the electric wires 28a.

The cylindrical housing 30 consists in the example of two parts, to facilitate the installation and servicing of the internal parts, which are connected with each other by a flange connection with threaded bolts 41. So that the liquid metal can be distilled-off in the device 6 itself under vacuum, the electric heater coil 27 is wound in the form of a helix around the outside of the housing 30, as already indicated above. As FIG. 2 makes clear, the heater coil 27 is wound in some regions with a different pitch in order to meet the different heat demands of the individual zones, such as is necessary to obtain an isothermal temperature pattern over the height of the device. Here, the pitch of the helix is largest in the vicinity of the crucibles 23, in the region below, the smallest, and in the region above, somewhat larger than in the lower region, in order to compensate for the heat convection. The same effect can be achieved, of course, also by using heater wires of different resistance (not shown) in the individual regions. It will also be seen from the drawing that all inside surfaces 45 of the housing 33 and 44 of the insert 31 which are not vertical, are made inclined downwardly, in order to avoid that after the crucibles 23 have been flushed out, liquid metal is left standing at these surfaces, which, by dropping into the crucibles 23, could falsify the analysis of the content or form, during the subsequent distillation, deposits which are hard to remove later.

The sealing between the housing 30 and the insert 31, is taken over by the sealing surfaces 46, which are clad with Stellite and of which at least one is made somewhat crowned or rounded, so that dirt that might be on them is pushed away when they are pressed together. A further seal is designated with 37, and the effectiveness of the seals can be monitored by means of one of the known leak detectors 42 for electrically conducting liquids, according to the induction principle. Finally, liquid metal that might have escaped into the gap between the housing 30 and the insert 31, can be frozen by a cooling device 43, not described in detail.

In order to ensure an exactly reproducible filling level, attention must be given that the mounts 36 and the bottom and the upper edge of the crucibles 23 are exactly horizontally plane-parallel.

The downwardly facing, annular concave surface 34, or baffle, has a conical depending part 34a which depends into the open top of the vertical feed line or pipe 4 which extends upwardly into the lower part of the housing 30 concentrically therewith, the baffle surface 34 being symmetrical and concentric with the axis of the feed pipe. The baffle surfaces are streamlined. As shown, the outer periphery of the baffle surface, namely, its run-off edge 35, extends radially beyond the outer periphery of the zone 47 and, therefore, beyond the outer extents of the crucibles, thus inducing turbulance in the crucibles when the liquid metal is deflected downwardly into them by the baffle. The degree and direction of turbulance of the liquid metal deflected into the crucibles, can be varied in the crucibles, by varying the offset direction and its extent, of the liquid metal run-off edge of the baffle.

The operation of the device is as follows:

Via the lines 1 and 4, liquid metal gets into the device 6, where it flows, deflected by the baffle surface 34, into the crucibles 23 in excess of their capacity. The excess then flows off through the line 24. After the flushing is completed, the supply and discharge of the liquid metal are interrupted by closing the valves 3 and 26 and the crucibles remain in place full, while it is assured by the particular design of the surfaces 34, 44, 45 that all excess liquid metal is removed from the housing 30 and flows through the line 13 into the buffer tank 8. Thereupon the insert 31 with the crucibles 23 suspended thereon is either pulled out (out-line operation) and brought into a manipulator box from where the crucibles alone are transported for analysis to the chemical laboratory, where the liquid metal is distilled off and the residue remaining in the crucibles 23 is chemically analyzed, or the liquid metal is distilled-off under vacuum in the device 6 (inline operation) and only the empty crucibles 23, which may contain residue, are transported to the laboratory in the manner described before.

What is claimed is:

1. A device for obtaining samples of liquid metal and comprising a housing having an inlet and an outlet for the liquid metal, and containing crucibles having open tops and which can be filled while in the housing with the liquid metal and subsequently removed from the housing; wherein the improvement comprises positioning means in said housing for positioning said crucibles so they form a horizontal ring of crucibles, said inlet comprising a vertical feed pipe extending upwardly in said housing within said ring of crucibles and having an open top for the upward ejection of the liquid metal at a level above the open tops of the ring of crucibles, and baffle means for forming a baffle surface spaced above the feed pipe's open top and the open tops of said ring of crucibles, said baffle surface being contoured to deflect liquid metal ejected upwardly from the feed pipe's open top, downwardly into the open tops of said ring of crucibles.

2. The device of claim 1 in which said housing has an open top and an upwardly removable insert normally closing the housing's open top, and means for connecting said baffle and said positioning means to said insert so that upward removal of the insert lifts said ring of crucibles from said housing.

3. The device of claim 1 in which said baffle surface is in the form of a downwardly facing annular concave surface having a periphery forming an annular run-off edge for liquid metal deflected downwardly into the open tops of said ring of crucibles.

4. The device of claim 3 in which the open tops of said ring of crucibles form an annular zone having radially inner and outer limits and said run-off edge extends over one of said limits.

5. The device of claim 1 in which said housing has a bottom up through which said feed pipe extends and in which said outlet is formed around said feed pipe, said housing having inside surfaces extending from said run-off edge to said outlet and all of said inside surfaces smoothly declining to avoid entrapment of the liquid metal on said inside surfaces.

6. The device of claim 3 in which said baffle surface has a central depending conical part with an apex positioned in the open top of said feed pipe to form therewith an annular liquid metal ejection opening leading to said annular concave surface.

7. The device of claim 2 in which said insert has an exposed top surface and includes radiation shielding material interposed between said baffle means and the insert's exposed top surface.

8. The device of claim 1 in which an electric heating coil having a non-uniform pitch encircles said housing in an area at least encompassing said positioning means for said ring of crucibles inside of the housing.

9. The device of claim 8 in which said coil extends above and below said area and said pitch is larger at said area and smaller above and below said area.

10. The device of claim 9 in which said pitch is larger above said area than it is below said area.

11. The device of claim 2 in which said insert and housing have Stellite clad inter-sealing surfaces.

12. The device of claim 11 in which at least one of said inter-sealing surfaces is crowned in shape.

13. The device of claim 1 having thermocouples soldered to said mounting means.

14. The device of claim 6 having a thermocouple positioned in said apex and signal wires extending from the thermocouple upwardly through said conical part.

* * * * *